US012774367B2

(12) United States Patent
Weber et al.

(10) Patent No.: US 12,774,367 B2
(45) Date of Patent: Oct. 27, 2026

(54) FUNCTIONALISED POLYGLYCINE-POLY(ALKYLENE IMINE)-COPOLYMERS, THE PREPARATION THEREOF AND USE THEREOF FOR PREPARING FORMULATIONS OF OR FOR COMPLEXING ANIONIC ACTIVE INGREDIENTS AND EFFECT SUBSTANCES

(71) Applicant: FRIEDRICH-SCHILLER-UNIVERSITÄT JENA, Jena (DE)

(72) Inventors: Christine Weber, Jena (DE); Natalie Göppert, Jena (DE); Ulrich S. Schubert, Jena (DE)

(73) Assignee: NGP POLYMERS GMBH, Jena (DE)

( * ) Notice: Subject to any disclaimer, the term of this patent is extended or adjusted under 35 U.S.C. 154(b) by 658 days.

(21) Appl. No.: 18/253,649

(22) PCT Filed: Nov. 19, 2021

(86) PCT No.: PCT/EP2021/000145
§ 371 (c)(1),
(2) Date: May 19, 2023

(87) PCT Pub. No.: WO2022/106048
PCT Pub. Date: May 27, 2022

(65) Prior Publication Data

US 2023/0416462 A1 Dec. 28, 2023

(30) Foreign Application Priority Data

Nov. 21, 2020 (DE) ......................... 102020007115.5

(51) Int. Cl.
*C08G 73/02* (2006.01)
*B82Y 5/00* (2011.01)
(Continued)

(52) U.S. Cl.
CPC ............ *C08G 73/0233* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

2017/0266224 A1 9/2017 Hedrick et al.

FOREIGN PATENT DOCUMENTS

CN 104024306 A 9/2014
CN 105821005 A 8/2016
EP 2800773 B1 * 12/2017

OTHER PUBLICATIONS

Chinese Office Action; 202180085606.8; Dated Jun. 14, 2025.
(Continued)

*Primary Examiner* — Tae H Yoon
(74) *Attorney, Agent, or Firm* — Dunlap Bennett & Ludwig PLLC; Anna L. Kinney

(57) ABSTRACT

Disclosed are copolymers comprising structural units of formula (I), of formula (II) and of formula (III)

—NR¹—CHR3—CHR4— (I),

—NH—CO—CHR⁷— (II),

—NH—CHR⁹—CHRf10— (III), or structural units of formula (IV), of formula (V) and of formula (VI)

—NR¹—CHR³—CHR⁴—CHR⁵— (IV),

—NH—CO—CHR⁷—CHR⁸ (V),

—NH—CHR⁹—CHR¹⁰—CHR¹¹— (VI), (Continued)

wherein
$R^1$ is a radical of formula —CO—$R^2$, of formula —CO—NH—$R^2$, of formula —$CH_2$—CH(OH)—$R^{12}$ or of formula —$CH_2$—CH($NH_2$)—$R^{12}$,
$R^3$, $R^4$, $R^5$, $R^7$, $R^8$, $R^9$, $R^{10}$ and $R^{11}$ independently of one another represent hydrogen, methyl, ethyl, propyl or butyl, and
$R^2$ and $R^{12}$ represent hydrogen or selected organic radicals. These copolymers are distinguished by a good degradability and can be used, for example, for the preparation of formulations containing active ingredients or for complexing anionic active ingredients or effect substances.

20 Claims, 4 Drawing Sheets

(51) Int. Cl.

| | |
|---|---|
| *B82Y 30/00* | (2011.01) |
| *B82Y 40/00* | (2011.01) |

(56) References Cited

OTHER PUBLICATIONS

International Search Report and Written Opinion; PCT/EP2021/000145; Mailed Mar. 14, 2022.

Englert, C, Hartlieb, M., Bellstedt, P., Kempe, K., Yang, C, Chu, S. K., Ke, X., García, J. M., Ono, R. J., Fevre, M., Wojtecki, R. J., Schubert, U. S., Yang, Y. Y., & Hedrick, J. L. (2015). Enhancing the biocompatibility and biodegradability of linear poly(ethylene imine) through controlled oxidation. Macromolecules, 48(20), 7420-7427. https://doi.org/10.1021/acs.macromol.5b01940.

Mees, M. A. & Hoogenboom, R. (2018). Full and partial hydrolysis of poly(2-oxazoline)s and the subsequent post- polymerization modification of the resulting polyethylenimine (co)polymers. Polymer Chemistry, 9(40), 4968-4978. https://doi.org/10.1039/c8py00978c.

International Search Report and Written Opinion; PCT/EP2021/000145; Issued May 16, 2023.

* cited by examiner

FUNCTIONALISED POLYGLYCINE-POLY(ALKYLENE IMINE)-COPOLYMERS, THE PREPARATION THEREOF AND USE THEREOF FOR PREPARING FORMULATIONS OF OR FOR COMPLEXING ANIONIC ACTIVE INGREDIENTS AND EFFECT SUBSTANCES

BACKGROUND

The invention relates to new copolymers which can be described as functionalized polyglycine-polyalkyleneimine copolymers characterized by very good degradability. In particular, the invention relates to the preparation and processing of these copolymers by oxidation of polyalkyleneimines followed by functionalization of NH groups in the partially oxidized polymer backbone. These copolymers can be used in particular for the preparation of active and effect substance formulations as well as for the complexation of anionic active and effect substances, in particular genetic material, such as siRNA, mRNA, DNA and CRISPR/Cas.

Biocompatible polymers represent highly attractive materials for biomedical applications such as drug delivery. Poly(ethylene glycol) (PEG) is currently the most widely used polymer for such purposes. Due to its high hydrophilicity and so-called “masking behavior,” it elicits little immune response in the body, thus increasing the blood circulation time of the drug. However, PEG has several disadvantages, namely the formation of toxic by-products, sequestration in organs, and stimulation of anti-PEG antibodies.

Poly(2-n-alkyl-2-oxazolines) (PAOx) with short side chains show similar hydrophilicity, biocompatibility and “masking behavior” and therefore seem to be promising candidates for a replacement of PEG, which was further confirmed in a detailed comparison of their dissolution behavior (cf. Grube, M.; Leiske, M. N.; Schubert, U. S.; Nischang, I. POx as an alternative to PEG? A hydrodynamic and light scattering study. *Macromolecules* 2018, 51, 1905-1916). Unlike PEG, PAOx also exhibit higher structural versatility due to their side-chain modifiability.

PAOx with longer side chains are hydrophobic and can be used to prepare amphiphilic copolymers, low surface energy materials, or low adhesion coatings. Thermal and crystalline properties can also be tailored by variations in the PAOx side chains (cf. Hoogenboom, R.; Fijten, M. W. M.; Thijs, H. M. L.; van Lankvelt, B. M.; Schubert, U. S. Microwave-assisted synthesis and properties of a series of poly(2-alkyl-2-oxazoline) s. *Des. Monomers Polym.* 2005, 8, 659-671; Rettler, E. F. J.; Kranenburg, J. M.; Lambermont-Thijs, H. M. L.; Hoogenboom, R.; Schubert, U. S. Thermal, mechanical, and surface properties of poly(2-N-alkyl-2-oxazoline) s *Macromol. Chem. Phys.* 2010, 211, 2443-2448; Kempe, K.; Lobert, M.; Hoogenboom, R.; Schubert, U. S. Synthesis and characterization of a series of diverse poly(2-oxazoline) s. *J. Polym. Sci., Part A: Polym. Chem.* 2009, 47, 3829-3838; Beck, M.; Birnbrich, P.; Eicken, U.; Fischer, H.; Fristad, W. E.; Hase, B.; Krause, H.-J. Polyoxazolines on a lipid chemical basis. *Angew. Makromol. Chem.* 1994, 223, 217-233; Rodríguez-Parada, J. M.; Kaku, M.; Sogah, D. Y. Monolayers and Langmuir-Blodgett films of poly(AT-acylethylenimines) with hydrocarbon and fluorocarbon side chains. *Macromolecules* 1994, 27, 1571-1577; Oleszko-Torbus, N.; Utrata-Wesołek, A.; Bochenek, M.; Lipowska-Kur, D.; Dworak, A.; Walach, W. Thermal and crystalline properties of poly(2-oxazoline) s. *Polym. Chem.* 2020, 11, 15-33; Demirel, A. L.; Tatar, G. P.; Verbraeken, B.; Schlaad, H.; Schubert, U. S.; Hoogenboom, R. Revisiting the crystallization of poly(2-alkyl-2-oxazoline) s. *J. Polym. Sci., Part B: Polym. Phys.* 2016, 54, 721-729). Schubert and colleagues previously reported a decrease in glass transition temperature ($T_g$) with increasing side chain length for a range of poly(2-n-alkyl-2-oxazolines) to poly(2-pentyl-2-oxazolines). For PAOx with longer side chains, crystalline properties with a melting temperature $T_m$ independent of side chain length were observed.

However, PAOx as well as PEG are considered non-biodegradable. For a variety of applications in biomedicine and other fields, biodegradability would be an important property, for example, to prevent polymers with molecular masses beyond 20,000 g $mol^{-1}$ from accumulating in the body and to remove the polymer completely from the organism. One strategy to solve the problem could be to integrate hydrolytically sensitive groups into the polymer backbone, e.g. ester or amide units. These can be hydrolyzed under, for example, acidic or enzymatic conditions, which could lead to degradation of the entire polymer. Several routes have already been investigated to incorporate ester groups into the PAOx backbone. Recently, the synthesis of a series of poly(esteramides) with lateral amide linkages prepared by organocatalytic ring-opening polymerization of N-acetylated-1,4-oxazepan-7-one monomers has been reported (ref. Wang, X.; Hadjichristidis, N. Organocatalytic ring-opening polymerization of N-acylated-1,4-oxazepan-7-ones toward well-defined poly(ester amide) s: biodegradable alternatives to poly(2-oxazoline) s. *ACS Macro Lett.* 2020, 9, 464-470). The resulting polymers can be considered as alternating poly(ester-co-oxazolines) and therefore as biodegradable PAOx alternatives. In the series of differentially degradable poly-(2-alkyl-2-oxazoline) and poly(2-aryl-2-oxazoline) analogs, all polymers exhibited amorphous behavior and showed lower $T_g$ compared to their non-degradable PAOx counterparts.

Recently, polymers consisting of the same repeating units synthesized by spontaneous zwitterionic copolymerization of 2-oxazoline and acrylic acid were reported to give N-acylated poly(amino ester) macromonomers. Downstream redox-initiated reversible addition-fragmentation chain transfer (RRAFT) polymerization of these macromonomers resulted in biodegradable comb polymers (cf. Kempe, K.; de Jongh, P. A.; Anastasaki, A.; Wilson, P.; Haddleton, D. M. Novel comb polymers from alternating N-acylated poly (aminoester) s obtained by spontaneous zwitterionic copolymerization. *Chem. Commun.* 2015, 51, 16213-16216; de Jongh, P. A. J. M.; Mortiboy, A.; Sulley, G. S.; Bennett, M. R.; Anastasaki, A.; Wilson, P.; Haddleton, D. M.; Kempe, K. Dual stimuli-responsive comb polymers from modular N-acylated poly(aminoester)-based macromonomers. *ACS Macro Lett.* 2016, 5, 321-325).

Other approaches used amidation of diethanolamine, resulting in different hydroxyethylsuccinamide monomers, followed by polycondensation of these monomers with succinic acid, aiming at similar polymer structures (cf. Swanson, J. P.; Monteleone, L. R.; Haso, F.; Costanzo, P. J.; Liu, T.; Joy, A. A library of thermoresponsive, coacervate-forming biodegradable polyesters. *Macromolecules* 2015, 48, 3834-3842; Gokhale, S.; Xu, Y.; Joy, A. A library of multifunctional polyesters with “peptide-like” pendant functional groups. *Biomacromolecules* 2013, 14, 2489-2493).

However, to the best of our knowledge, no attempts have been made to introduce amide bonds into a polyoxazoline backbone or into a backbone of other functionalized polyalkylene imines for the purpose of improving degradability.

SUMMARY

It is therefore an objective of the present invention to provide new functionalized copolymers with improved degradability.

A further objective of the present invention is to provide a simple method for the preparation of these functionalized copolymers.

This objective is solved by providing copolymers containing 5 to 75 mol % of structural units of the formula (I), 5 to 75 mol % of structural units of the formula (II) and 20 to 90 mol % of structural units of the formula (III)

$$—NR^1—CHR^3—CHR^4— \quad (I),$$

$$—NH—CO—CHR^7— \quad (II),$$

$$—NH—CHR^9—CHR^{10}— \quad (III),$$

or of copolymers containing 5 to 75 mol % of structural units of the formula (IV), 5 to 75 mol % of structural units of the formula (V) and 20 to 90 mol % of structural units of the formula (VI)

$$—NR^1—CHR^3—CHR^4—CHR^5— \quad (IV),$$

$$—NH—CO—CHR^7—CHR^8— \quad (V),$$

$$—NH—CHR^9—CHR^{10}—CHR^{11}— \quad (VI),$$

wherein $R^1$ is a radical of the formula $—CO—R^2$, of the formula $—CO—NH—R^2$, of the formula $—CH_2—CH(OH)—R^{12}$ or of the formula $—CH_2—CH(NH_2)—R^{12}$ $R^3$, $R^4$, $R^5$, $R^7$, $R^8$, $R^9$, $R^{10}$ and $R^{11}$ independently of one another are hydrogen, methyl, ethyl, propyl or butyl, $R^2$ is selected from the group consisting of hydrogen, alkyl, cycloalkyl, aryl, aralkyl, $—C_mH_{2m}—X$ or $—(C_nH_{2n}—O)_o—(C_pH_{2p}—O)_q—R^6$, $R^6$ is hydrogen or $C_1$-$C_6$ alkyl, $R^{12}$ is selected from the group consisting of hydrogen, alkyl, alkenyl, cycloalkyl, aryl or aralkyl, X is selected from the group consisting of hydroxyl, alkoxy, amino, N-alkylamino, N, N-dialkylamino, heterocyclyl having at least one ring nitrogen atom, guanidino, carboxyl, carboxylic acid ester, sulfuric acid ester, sulfonic acid ester or carbamic acid ester, m is an integer from 1 to 18, n and p independently of one another are integers from 2 to 4, where n is not equal to p, and and q independently of one another are integers from 0 to 60, at least one of o or q not being equal to 0, the percentages being based on the total amount of the structural units of the formula (I), (II) and (III) or of the formula (IV), (V) and (VI).

These copolymers can be prepared starting from readily accessible poly(alkylene imines).

Therefore, the invention also relates, in a first variant, to a process for the preparation of these copolymers comprising the steps of i) reacting a polyalkyleneimine containing recurring structural units of formula (Ia) or of formula (IVa), preferably in an amount of at least 90 mol %, with an oxidizing agent, thereby obtaining a copolymer containing the structural units of formula (Ia) and of formula (II) or containing the structural units of formula (IVa) and of formula (V)

$$—NH—CR^3H—CR^4H— \quad (Ia),$$

$$—NH—CO—CR^7H— \quad (II),$$

$$—NH—CR^3H—CR^4H—CR^5H— \quad (IVa),$$

$$—NH—CO—CR^7H—CR^8H— \quad (V),$$

wherein $R^3$, $R^4$, $R^5$, $R^7$ and $R^8$ have the meaning defined above, and ii) reacting the copolymer of step i) with an acyl derivative of the formula (VII) or with an isocyanate of the formula (VIII) or with an epoxide of the formula (IX) or with an aziridine of the formula (X) to give a copolymer containing the structural units defined above of the formulae (I), (II) and (III) or of the formulae (IV), (V) and (VI)

$$R^2—CO—R^{13}, \quad (VII)$$

$$R^2—NCO, \quad (VIII)$$

(IX)

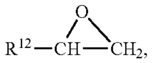

(X)

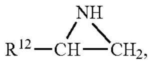

wherein $R^2$ and $R^{12}$ have the meaning defined above, and $R^{13}$ represents a leaving group, in particular fluorine, chlorine, bromine, iodine or another leaving group of an activated carboxylic acid derivative.

Furthermore, in a second embodiment, the invention relates to a process for the preparation of these copolymers, comprising the steps of iii) partial hydrolysis of a polyoxazoline containing recurring structural units of formula (I) or a polyoxazine containing recurring structural units of formula (IV)

$$—NR^1—CHR^3—CHR^4— \quad (I),$$

$$—NR^1—CHR^3—CHR^4—CHR^5— \quad (IV),$$

to give a copolymer containing the recurring structural units of formula (I) and of formula (III) or of formula (IV) and of formula (VI)

$$—NH—CHR^9—CHR^{10}— \quad (III),$$

$$—NH—CHR^9—CHR^{10}—CHR^{11}— \quad (VI),$$

wherein $R^1$, $R^3$, $R^4$, $R^5$, $R^9$, $R^{10}$ and $R^{11}$ have the meaning defined above, and iv) reacting the copolymer from step iii) with an oxidizing agent, thereby obtaining a copolymer containing the structural units of formula (I), of formula (II) and of formula (III) or containing the structural units of formula (IV), of formula (V) and of formula (VI)

$$—NH—CO—CHR^7— \quad (II),$$

$$—NH—CO—CHR^7—CHR^8— \quad (V),$$

wherein $R^7$ and $R^8$ have the meaning defined above.

According to the invention, it was found that degradable functionalized polyglycine-polyalkyleneimine copolymers with amide linkages integrated into the polymer backbone can be prepared via a simple synthetic route. To this end, polyalkyleneimines can be partially oxidized and the resulting product can be functionalized via reaction with an epoxide, an aziridine, an isocyanate, or an activated ester or acyl halide. In an alternative synthetic route, polyoxazolines or polyoxazines can be partially hydrolyzed to give polyalkyleneimine units, which can be partially oxidized in a subsequent step.

Polyalkyleneimines used in the first variant of the process according to the invention usually contain at least 90 mol % of recurring structural units of formula (Ia) or formula (IVa) and are commercially available or can be obtained by hydrolysis of poly(2-oxazolines) (POx) substituted in the 2-position, in particular of PEtOx, or of poly(2-oxazines) substituted in the 2-position.

POx containing at least 20 mol %, preferably at least 50 mol %, of recurring structural units derived from 2-oxazoline in the polymer are usually used as starting materials for hydrolysis. While commercially available polyalkyleneimines are branched, linear polyalkyleneimines are obtained by hydrolysis of POx.

In a second variant of the process according to the invention, hydrolysis of polyoxazolines or polyoxazines can also be partial and leads to copolymers containing recurring structural units of the formulae (I) and (III) or containing recurring structural units of the formulae (IV) and (VI). These copolymers can be oxidized, leading directly to the copolymers of the invention. In this process variant, reacylation is usually omitted.

DETAILED DESCRIPTION

Figure 1:
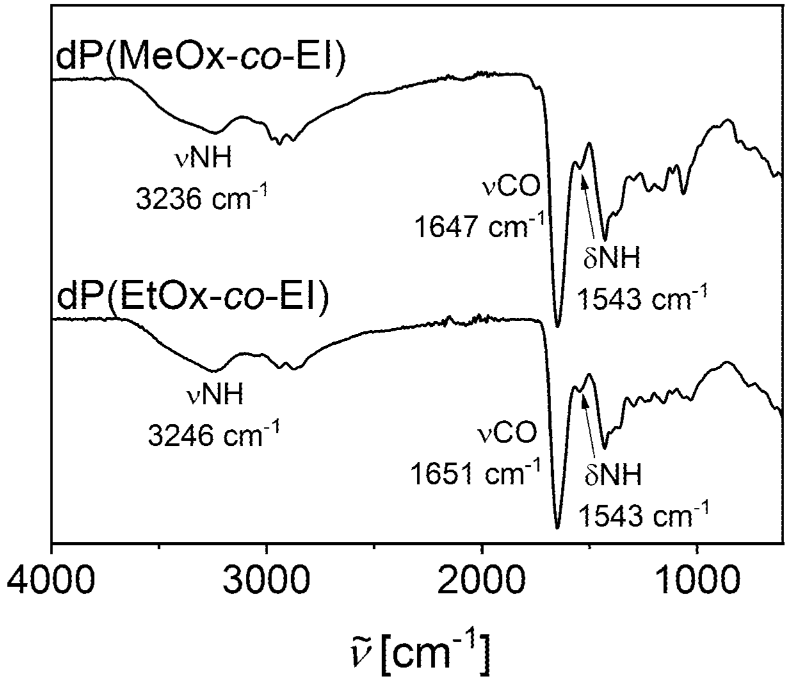
FIG. 1 is a graph of ATR-IR spectra of dP(MeOx-co-EI) and dP(EtOx-co-EI) as described in Example C2.

A preferred simple synthetic route of post-polymerization is via the consecutive hydrolysis of poly(2-ethyl-2-oxazoline) (PEtOx), a partial oxidation and reacylation. The use of PEtOx or corresponding poly(2-alkyl-2-oxazolines) as well-defined starting materials is advantageous, since these polymers can be obtained by cationic ring-opening polymerization (CROP) of commercially available monomers. The subsequent hydrolysis of PEtOx or corresponding poly(2-alkyl-2-oxazolines) under acidic conditions, leading to linear poly(ethyleneimine) (PEI), is well studied and known to those skilled in the art and can also be partially carried out. However, PEI is disadvantageous because of its cytotoxicity and, like PEtOx, its nondegradability. Englert et al. reported the controlled oxidation of linear PEI with hydrogen peroxide to enhance degradability by including amide groups in the PEI backbone (compare Enhancing the biocompatibility and biodegradability of linear poly(ethylene imine) through controlled oxidation; *Macromolecules* 2015, 48, 7420-7427). The resulting structure corresponds to the repeat unit of poly(glycine) and therefore the polymer can be considered as poly(ethyleneimine-co-glycine) (here referred to as oxPEI). Due to its additional hydrolytically sensitive amide groups, the polymer showed not only increased degradability but also improved biocompatibility compared to the otherwise cytotoxic PEI.

According to the invention, oxPEI was functionalized with a subsequent reacylation step or by reaction with isocyanates or with epoxides or with aziridines. Accordingly, the homologous polypropyleneimine (PPI) can be used instead of PEI. Reacylation of oxPEI with acylating reagents, such as acyl halides, allowed the preparation of poly(2-n-alkyl-2-oxazoline-stat-glycine) (referred to here as dP(AOx-co-EI)). Due to the presence of additional amide groups in the polymer backbone, it was suspected and also experimentally demonstrated that the resulting dP(AOx-co-EI) exhibited enhanced degradability compared to their poly(2-n-alkyl-2-oxazoline) equivalents. Similar acylation reactions of PEI with activated carboxylic acid derivatives, such as acyl chlorides, anhydrides, or N-hydroxysuccinimide esters, have been reported previously in various ways (compare Mees, M. A.; Hoogenboom, R. Functional poly (2-oxazoline) s by direct amidation of methyl ester side chains. *Macromolecules* 2015, 48, 3531-3538; Sedlacek, O.; Monnery, B. D.; Hoogenboom, R. Synthesis of defined high molar mass poly(2-methyl-2-oxazoline). *Polym. Chem.* 2019, 10, 1286-1290; Englert, C.; Tauhardt, L.; Hartlieb, M.; Kempe, K.; Gottschaldt, M.; Schubert, U. S. Linear poly (ethylene imine)-based hydrogels for effective binding and release of DNA. *Biomacromolecules* 2014, 15, 1124-1131; Englert, C.; Trutzschler, A. K.; Raasch, M.; Bus, T.; Borchers, P.; Mosig, A. S.; Traeger, A.; Schubert, U. S. Crossing the blood-brain barrier: glutathione-conjugated poly(ethylene imine) for gene delivery. *J. Controlled Release* 2016, 241, 1-14; and Englert, C.; Prohl, M.; Czaplewska, J. A.; Fritzsche, C.; Preussger, E.; Schubert, U. S.; Traeger, A.; Gottschaldt, M. D-Fructose-decorated poly(ethylene imine) for human breast cancer cell targeting. *Macromol. Biosci.* 2017, 17, 1600502).

Re-functionalization of oxPEI or oxidized poly(propylene imine) (oxPPI) has not yet been described.

During re-functionalization, the amount of acyl derivative of formula (VII) or of isocyanate of formula (VIII) or of epoxide of formula (IX) or of aziridine of formula (X) should be chosen such that the proportion of structural units of formula (III) or of formula (VI) in the resulting copolymer is between 20 and 90 mol %.

In the context of the present description, "copolymers" means the above-mentioned organic compounds characterized by the repetition of certain units (monomer units or repeating units). The copolymers according to the invention consist of at least three types of different repeating units. Polymers are produced by the chemical reaction of monomers with the formation of covalent bonds (polymerization) and form the so-called polymer backbone by linking the polymerized units. This can have side chains on which functional groups can be located. Copolymers according to the invention consist of at least three different monomer units, which can be arranged randomly, as a gradient, alternately or as a block. If the copolymers possess partly hydrophobic properties, they can form nanoscale structures (e.g. nanoparticles, micelles, vesicles) in an aqueous environment.

In the context of the present description, "water-soluble compounds" or "water-soluble copolymers" are compounds or copolymers that dissolve to at least 1 g/L water at 25° C.

In the context of the present description, "active ingredients" are compounds or mixtures of compounds that exert a desired effect on a living organism. These may be, for example, pharmaceutical active ingredients or agrochemical active ingredients. Active ingredients may be low or high molecular weight organic compounds. Preferably, the active ingredients are higher molecular weight pharmaceutically active substances, whereby hydrophilic active ingredients from nucleic acids, in particular from potentially therapeutically useful nucleic acids (e.g. small interfering RNA, short hairpin RNA, micro RNA, plasmid DNA) are of particular interest.

The term “active pharmaceutical ingredient” as used herein means any inorganic or organic molecule, substance or compound that exhibits a pharmacological effect. The term “active pharmaceutical ingredient” is used herein synonymously with the term “drug”.

In the context of the present description, the term “effect substances” is understood to mean compounds or mixtures of compounds which are added to a formulation in order to give it certain additional properties and/or to facilitate its processing. The terms “effect substances” and “auxiliaries and additives” are used synonymously in the context of this description.

In the context of the present description, “auxiliaries and additives” are substances that are added to a formulation to give it certain additional properties and/or to facilitate its processing. Examples of auxiliaries and additives are tracers, contrast agents, carriers, fillers, pigments, dyes, perfumes, lubricants, UV stabilizers, antioxidants or surfactants. In particular, “auxiliaries and additives” are to be understood as any pharmacologically compatible and therapeutically useful substance which is not a pharmaceutically active ingredient but which can be formulated together with a pharmaceutically active ingredient in a pharmaceutical composition in order to influence, in particular improve, qualitative properties of the pharmaceutical composition. Preferably, the auxiliaries and/or additives do not exert any pharmacological effect or, with regard to the intended treatment, no appreciable pharmacological effect or at least no undesirable pharmacological effect.

In the context of the present description, “polymer particles” means copolymers according to the invention in particle form, which may also contain other ingredients. The particles may be present in liquid form dispersed in a hydrophilic liquid or the particles may be present in solid form, either dispersed in a hydrophilic liquid or in the form of a powder. The size of the particles can be determined by visual methods, such as microscopy; for particle sizes in the nanoscale, light scattering or electron microscopy can be used. The shape of the polymer particles can be arbitrary, for example spherical, ellipsoidal or irregular. The polymer particles can also form aggregates of several primary particles. Preferably, the particles of copolymers according to the invention are in the form of nanoparticles. The particles may contain other components in addition to the copolymers, for example active ingredients or auxiliaries or additives.

The terms “particles” or “corpuscles” are used synonymously in the context of the present description.

In the context of the present description, the term “nanoparticles” refers to particles whose diameter is less than 1 μm and which may be composed of one or more molecules. They are generally characterized by a very high surface-to-volume ratio and thus offer very high chemical reactivity. Nanoparticles can consist of copolymers according to the invention or contain other components in addition to these copolymers, such as active ingredients or auxiliaries or additives.

The copolymers according to the invention can be present as linear polymers or they can also be branched copolymers. Linear copolymers are formed, for example, by consecutive hydrolysis of PEtOx, followed by partial oxidation to oxPEI and by reacylation to dP(AOx-co-EI). Branched copolymers are formed, for example, by partial oxidation of commercially available PEI, which is known to be branched, to oxPEI followed by re-functionalization, e.g., by reacylation to dP(AOx-co-EI).

The solubility of the copolymers according to the invention can be influenced by co-polymerization with suitable monomers and/or by functionalization. Such techniques are known to the skilled person.

The copolymers according to the invention can comprise a wide range of molar masses. Typical molar masses ($M_n$) range from 1,000 to 500,000 g/mol, in particular from 1,000 to 50,000 g/mol. These molar masses can be determined by $^1$H NMR spectroscopy of the dissolved polymer. In particular, an analytical ultracentrifuge or chromatographic methods, such as size exclusion chromatography, can be used to determine the molar masses.

Preferred copolymers according to the invention have an average molecular weight (number average) in the range from 1,000 to 50,000 g/mol, in particular from 3,000 to 20,000 g/mol, determined by $^1$H-NMR spectroscopy or by using an analytical ultracentrifuge. Preferably, these are linear copolymers. Branched copolymers according to the invention preferably have a higher average molar mass, for example an $M_n$ in the range from 50,000 to 500,000 g/mol, in particular from 80,000 to 200,000 g/mol.

The molar proportion of structural units of the formula (I) in the copolymers according to the invention is from 5 to 75 mol %, preferably from 20 to 60 mol %, based on the total amount of structural units of the formulae (I), (II) and (III).

The molar proportion of structural units of the formula (II) in the copolymers according to the invention is 5 to 75 mol %, preferably 10 to 60 mol %, based on the total amount of structural units of the formulae (I), (II) and (III).

The molar proportion of structural units of the formula (III) in the copolymers according to the invention is 20 to 90 mol %, preferably 21 to 90 mol %, and in particular 30 to 80 mol %, based on the total amount of structural units of the formulae (I), (II) and (III).

The molar proportion of structural units of the formula (IV) in the copolymers according to the invention is 5 to 75 mol %, preferably 20 to 60 mol %, based on the total amount of structural units of the formulae (IV), (V) and (VI).

The molar fraction of structural units of the formula (V) in the copolymers according to the invention is 5 to 75 mol %, preferably 10 to 60 mol %, based on the total amount of structural units of the formulae (IV), (V) and (VI).

The molar proportion of structural units of the formula (VI) in the copolymers according to the invention is 20 to 90 mol %, preferably 21 to 90 mol %, and in particular 30 to 80 mol %, based on the total amount of structural units of the formulae (IV), (V) and (VI).

$R^1$ is a radical of the formula —CO—$R^2$ or of the formula —CO—NH—$R^2$ or of the formula —$CH_2$—CH(OH)—$R^{12}$ or of the formula —$CH_2$—CH($NH_2$)—$R^{12}$, preferably a radical of the formula —CO—$R^2$.

$R^3$, $R^4$, $R^5$, $R^7$, $R^8$, $R^9$, $R^{10}$ and $R^{11}$ independently of one another denote hydrogen, methyl, ethyl, propyl or butyl, preferably hydrogen, methyl or ethyl and in particular hydrogen.

$R^2$ is hydrogen, alkyl, cycloalkyl, aryl, aralkyl, —$C_mH_{2m}$—X or —$(C_nH_{2n}—O)_o$—$(C_pH_{2p}—O)_q$—$R^6$, preferably hydrogen, $C_1$-$C_{18}$-alkyl, cyclohexyl or phenyl, in particular $C_1$-$C_{18}$-alkyl and very preferably $C_4$-$C_{14}$-alkyl.

$R^6$ is hydrogen or $C_1$-$C_6$-alkyl, preferably hydrogen or methyl $R^{12}$ is hydrogen, alkyl, alkenyl, cycloalkyl, aryl or aralkyl, preferably hydrogen, $C_1$-$C_{18}$-alkyl, $C_2$-$C_{18}$-alkenyl, cyclohexyl or phenyl, in particular hydrogen, $C_1$-$C_6$-alkyl or $C_2$-$C_3$-alkenyl.

m is an integer from 1 to 18, preferably from 2 to 12.

X is hydroxyl, alkoxy, amino, N-alkylamino, N,N-dialkylamino, heterocyclyl having at least one ring nitrogen atom, guanidino, carboxyl, carboxylic acid ester, sulfuric acid ester, sulfonic acid ester or carbamic acid ester.

In the context of this description, a heterocyclyl group is a cyclic saturated or unsaturated monovalent radical having from five to seven ring atoms, of which from one to three of the ring atoms are heteroatoms other than carbon, at least one of which is a nitrogen atom, preferably heteroatoms selected from the group consisting of nitrogen, oxygen or sulfur, and wherein the remaining ring atoms are carbon atoms. Heterocyclyl groups may also form ring systems with two or more heterocyclic rings linked by covalent bonds, such as bipyridyl radicals, or which are fused, such as indenyl radicals. Furthermore, heterocyclyl groups may be ring systems in which one or more heterocyclic rings occur that are linked to hydrocarbon rings, such as benzimidazole rings. Heterocyclyl groups can be aromatic or non-aromatic.

Heterocyclyl groups can consist of a ring. Examples include piperidinyl, pyridyl, morpholinyl, or imidazolyl radicals.

Heterocyclyl groups may consist of multiple rings. Examples are benzimidazole or indenyl radicals.

n and p are independently integers from 2 to 4, where n is not equal to p. Preferably, n is 2 and p is 3.

o and q are independently integers from 0 to 60, where at least one of o or q is not 0. Preferably, o and q are, independently of one another, 1 to 40, in particular 2 to 10.

The radicals $R^2$ and $R^{12}$ can denote alkyl. These are usually alkyl groups with one to twenty carbon atoms, which can be straight-chain or branched. Examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or eicosyl. Methyl, ethyl and propyl are preferred.

Radical $R^{12}$ can mean alkenyl. These are usually alkenyl groups with two to twenty carbon atoms, which may be straight-chain or branched. The double bond can be at any position in the chain, but preferably in the alpha position. Examples of alkenyl radicals are vinyl, allyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl or eicosenyl. Vinyl and allyl are particularly preferred.

The radicals $R^2$ and $R^{12}$ can denote cycloalkyl. These are usually cycloalkyl groups with five to six ring carbon atoms. Cyclohexyl is particularly preferred.

The radicals $R^2$ and $R^{12}$ can denote aryl. These are generally aromatic hydrocarbon radicals having five to ten ring carbon atoms. Preferred is phenyl.

The radicals $R^{22}$ and $R^{12}$ can denote aralkyl. These are usually aryl groups linked to the rest of the molecule through an alkylene group. Preferred is benzyl.

Radical X can mean alkoxy. These are usually $C_1$-$C_6$-alkoxy groups. Preferred is ethoxy and especially methoxy.

Radical X can mean amino, N-alkylamino or N, N-dialkylamino. The alkyl groups are usually $C_1$-$C_6$-alkyl groups. Preferred is ethyl and in particular methyl.

Radical X can mean heterocyclyl with at least one ring nitrogen atom. Preferred are piperidinyl, pyridyl, pyrimidinyl, purinyl, morpholinyl, imidazolyl, benzimidazolyl, adeninyl, guaninyl, cytosinyl, thyminyl or uracilyl.

Radical X may be a carboxylic acid ester (—COOR), sulfonic acid ester (—$SO_3$R), sulfuric acid ester (—$SO_4$R) or carbamic acid ester (—NR COOR or —OCONRR') (R and R' are each monovalent organic radicals). These are usually esters of carboxylic, sulfonic, sulfuric or carbamic acids with aliphatic alcohols, in particular with aliphatic $C_1$-$C_6$-alcohols. Ethyl and in particular methyl esters are preferred.

Preferred are copolymers containing 15 to 60 mol % of structural units of the formula (I), 10 to 60 mol % of structural units of the formula (II) and 25 to 75 mol % of structural units of the formula (III).

Also preferred are copolymers in which $R^1$ is a radical of the formula —CO—$R^2$.

Also preferred are copolymers in which $R^2$ is $C_1$-$C_{18}$-alkyl, in particular $C_1$-$C_6$-alkyl, and very preferably C1-$C_2$-alkyl.

Further preferred are copolymers in which $R^2$ is C3-$C_{18}$-alkyl, in particular C7-$C_{12}$-alkyl.

A further group of preferred copolymers is characterized in that $R^2$ is $C_1$-$C_{18}$-alkyl and $R^3$, $R^4$, $R^5$, $R^7$, $R^8$, $R^9$, $R^{10}$ and $R^{11}$ are hydrogen.

Furthermore, copolymers in which $R^6$ is hydrogen or methyl are preferred.

Further preferred copolymers are characterized in that $R^{12}$ is $C_1$-$C_{18}$-alkyl or $C_2$-$C_{18}$-alkenyl, in particular methyl, ethyl, vinyl or allyl.

Further preferred copolymers are characterized in that n=2 and p=3.

The copolymers of the invention may consist of the structural units of the formulae (I), (II) and (III) or of the structural units of the formulae (IV), (V) and (VI) or may additionally contain further structural units derived from monomers which can be copolymerized with monomers used in the preparation of polyalkyleneimines or polyoxazolines. The proportion of such further structural units, based on the total mass of the copolymer, is generally up to 25 mol %. These further structural units can be randomly distributed or arranged in the form of blocks in the copolymer.

Preferred copolymers according to the invention are characterized in that they contain at least 90 mol %, in particular at least 95 mol %, based on their total mass, of structural units of the formula (I), the formula (II) and the formula (III) or of the formula (IV), the formula (V) and the formula (VI).

The copolymers according to the invention have end groups that are typically formed during the preparation of poly(oxazolines) or poly(alkylenimines). These end groups can be modified by functionalization. The techniques required for this are known to the skilled person.

Examples of omega end groups of the polyoxazoline or polyoxazine starting materials of the copolymers of the invention are halogen atoms, such as fluorine, chlorine, bromine or iodine; or azide groups —$N_3$; or fluoro (alkyl) sulfonic acid ester groups, such as the nonaflate group —$OSO_2C_4F_9$, the trifluoromethane sulfonate group —$OSO_2CF_3$ or the fluorosulfonate group —$OSO_2F$; or aryl or alkylsulfonic acid groups, such as the tosyl group $CH_3$—$C_6H_4$—$SO_2$— or the mesyl group $CH_3$—$SO_2$—; the unsubstituted, mono- or di-substituted amino group $NH_2$, —NHR or —$NR_2$ (where R=monovalent organic radical), the hydroxyl group OH, the thiol group —SH, or the ester group —OCOR, the thioester group —SCOR; the phthalimide group or the cyano group —CN, and other functional groups obtainable by modification of these end groups. The copolymers according to the invention contain these residues as end groups or may contain the hydrolysis and/or oxidation products of these residues as end groups.

Copolymers according to the invention can be covalently linked to other active or effect substances via the end groups.

The copolymers according to the invention can be prepared—as disclosed above—by partial oxidation of polyalkyleneimines and by re-functionalization of the oxidized product by reaction with an epoxide, aziridine, isocyanate, an activated carboxylic acid or an acyl halide.

The oxidation is preferably carried out in solution, in particular in aqueous or alcoholic-aqueous solution. Oxidants known per se can be used as oxidizing agents. Examples include per compounds, hypochlorites, chlorine or oxygen, in particular hydrogen peroxide.

Preferably, per-compounds are used. Examples are hydrogen peroxide, peracids, organic peroxides or organic hydroperoxides, in particular hydrogen peroxide.

Preferred processes are those in which the oxidizing agent used is hydrogen peroxide.

The amount of oxidizing agent is selected so that the desired proportion of oxidized structural units is formed in the polymer backbone.

The reaction temperature is generally between 1° and 80° C., particularly in the range of 20 to 40° C.

The reaction time for oxidation is generally between 5 minutes and 5 days.

Re-functionalization of the oxidized product is carried out by reaction with an acyl derivative of formula (VII) described above or with an isocyanate of formula (VIII) described above, or with an epoxide of formula (IX) described above or with an aziridine of formula (X) described above.

Examples of suitable acyl derivatives are acyl halides, carboxylic acid anhydrides or carboxylic acids activated by means of known coupling reagents, for example N-hydroxysuccinimide esters (NHS esters), dicyclohexylcarbodiimide esters (DCC esters) or 1-ethyl-3-(3-dimethylaminopropyl) carbodiimide esters (EDC esters).

Examples of suitable isocyanates are monoalkyl isocyanates, such as methane isocyanate or ethane isocyanate, cyclohexyl isocyanate or phenyl isocyanate.

Examples of suitable epoxides are ethylene oxide, propylene oxide, 1,2-epoxybut-3-ene or 1,2-epoxypent-4-ene.

Examples of suitable aziridines are azacyclopropane, 1,2-azapropane, 1,2-azabut-3-ene or 1,2-azapent-4-ene.

The reaction temperature is generally between 1° and 80° C., in particular in the range of 20 to 40° C.

The reaction time during re-functionalization is generally between 5 minutes and 5 days, in particular between 12 and 48 hours.

Preferably, the poly(alkyleneimines) used are copolymers obtained by alkaline hydrolysis or, in particular, by acid hydrolysis of poly(2-oxazolines), especially poly(2-alkyl-2-oxazolines). These copolymers are linear and are used as well-defined starting materials derived from polymers that can be obtained by CROP of commercially available monomers.

Poly(oxazolines) are well-known compounds. These are usually prepared by cationic ring-opening polymerization of 2-oxazolines in solution and in the presence of an initiator. Examples of initiators include electrophiles, such as esters of aromatic sulfonic acid salts or esters of aliphatic sulfonic acids or carboxylic acids, or aromatic halogen compounds. Multi-functional electrophiles can also be used as initiators. In addition to linear poly(oxazoline) s, branched or star-shaped molecules can also be formed. Examples of preferred initiators are esters of arylsulfonic acids, such as methyl tosylate, esters of alkanesulfonic acids, such as methyl triflate, or mono- or dibromomethylbenzene. The polymerization is usually carried out in a polar aprotic solvent, for example in acetonitrile.

The oxazolines used for the preparation of the poly (oxazolines) according to the invention are 2-oxazolines (4,5-dihydrooxazoles) with a C═N double bond between the carbon atom 2 and the nitrogen atom. These may be substituted at the 2-, 4- and/or 5-carbon atom, preferably at the 2-carbon atom.

Preferably, 2-oxazolines are used which contain a substituent at the 2-position. Examples of such substituents are methyl or ethyl.

In addition to 2-oxazolines, other monomers copolymerizable with 2-oxazolines can be used in the preparation of the poly(oxazolines) used as starting materials according to the invention.

Instead of oxazolines, 2-oxazines can also be used to prepare homologous poly(oxazines).

The hydrolysis of poly(oxazolines) is preferably carried out in solution, in particular in aqueous or alcoholic-aqueous solution. Inorganic or organic acids can be used as acids. Preferably, mineral acids are used. Examples are hydrochloric acid, sulfuric acid or nitric acid, preferably hydrochloric acid. Suitable bases include alkali hydroxides, such as sodium hydroxide or potassium hydroxide.

The reaction temperature is generally between 2° and 180° C., especially in the range of 70 to 130° C.

The reaction time for acid hydrolysis is generally between 5 minutes and 24 hours.

Preference is thus given to processes in which the polyalkyleneimine used in step i) is obtained by hydrolysis, in particular by acid hydrolysis of a poly(oxazoline).

The copolymers according to the invention can be used for the preparation of formulations containing pharmaceutical or agrochemical active ingredients.

As a result of their good biodegradability, they are ideally suited for applications in the field of drug delivery. These uses are also within the scope of the present invention.

The copolymers according to the invention can be water-soluble or non-water-soluble depending on their functionalization. Copolymers functionalized with formyl, acetyl-propionyl or butionyl groups are generally water soluble. Copolymers functionalized with longer alkanoyl chains, on the other hand, are not water-soluble.

Non-water-soluble copolymers according to the invention can be present dispersed in hydrophilic liquids, for example as emulsions or as suspensions.

Preferably, the copolymers according to the invention are in the form of particles, in particular in the form of nanoparticles.

The invention therefore also relates to particles, in particular nanoparticles comprising the copolymers described above.

Preferred are nanoparticles whose average diameter $D_{50}$ is less than 1 μm, preferably 20 to 500 nm.

Particles containing one or more pharmaceutical or agrochemical active ingredients are particularly preferred.

Particularly preferred particles contain, in addition to the copolymer of the invention, at least one pharmaceutically active ingredient and suitable auxiliaries and additives.

The particles may be present as a powder in solid form or they may be present dispersed in hydrophilic solvents, the particles being present in the dispersing medium in liquid form or, in particular, in solid form.

Preferably, the particles form a disperse phase in a liquid containing water and/or water-miscible compounds.

The proportion of particles in a dispersion can cover a wide range. Typically, the proportion of particles in the dispersion medium is 0.5 to 20 wt %, preferably 1 to 5 wt %.

The particles according to the invention can be prepared by precipitation, preferably by nanoprecipitation. For this purpose, the copolymers according to the invention, which are little or not hydrophilic due to the presence of hydrophobic groups, are dissolved in a water-miscible solvent, such as acetone. This solution is dropped into a hydrophilic dispersing medium. This is preferably done with vigorous stirring. This can promote the production of smaller particles. The copolymer is deposited in the dispersing medium in finely divided form.

Alternatively, the particles according to the invention can also be produced by emulsification, preferably by nanoemulsion. For this purpose, the copolymers according to the invention, which are little or not hydrophilic due to the presence of hydrophobic groups, are dissolved in a water-immiscible solvent, such as dichloromethane or ethyl acetate. This solution is combined with a hydrophilic dispersing medium, preferably forming two liquid phases. This mixture is then emulsified by energy input, preferably by sonication with ultrasound.

In addition to the copolymer according to the invention, one or more active ingredients and/or one or more auxiliary substances and additives may be present during its dispersion in the dispersion medium. Alternatively, these active ingredients and/or auxiliary substances and additives may be added after the copolymer has been dispersed in the hydrophilic liquid.

The separation of the polymer particles from the hydrophilic liquid can be carried out in various ways. Examples include centrifugation, ultrafiltration or dialysis.

The polymer dispersion produced according to the invention can be further purified after production. Common methods include purification by dialysis, by ultrafiltration, by filtration or by centrifugation.

The copolymers according to the invention can be used excellently for complex formation with anionic compounds. Such complexes may be in the dissolved form, but preferably in the form of particles and in particular in the form of nanoparticles.

The invention therefore also relates to complexes of the copolymers described above and compounds with anionic groups, for example with carboxyl groups, sulfate groups, sulfonate groups or phosphate groups.

The invention also relates to particles, in particular nanoparticles containing complexes of the copolymers described above and compounds with anionic groups, for example with carboxyl groups, sulfate groups, sulfonate groups or phosphate groups.

In particular, nucleic acids or proteins can be used as compounds with anionic groups.

Particularly preferably, the present invention relates to particle-containing complexes formed from nucleic acids and the copolymers containing the structural units of the formulae (I), (II) and (III) described above or of the formulae (IV), (V) and (VI).

In the complexes and particles according to the invention, DNA and/or RNA and modifications thereof can be used as nucleic acids.

Any DNA types can be used. Examples include A-DNA, B-DNA, Z-DNA, mtDNA, antisense DNA, bacterial DNA and viral DNA.

Any RNA types can also be used. Examples include hnRNA, mRNA, tRNA, rRNA, mtRNA, snRNA, snoRNA, scRNA, siRNA, miRNA, antisense RNA, bacterial RNA and viral RNA.

Combinations of DNA and RNA can also be used in the complexes and particles of the invention.

It is assumed that the particles according to the invention contain nucleic acid copolymer complexes which are distributed over the entire volume of the particle. In contrast to previously known particles with a pronounced core-shell structure and with a concentration of the nucleic acid-polymer complexes in the outer shell, in the particles according to the invention nucleic acid-copolymer complexes are found both in the interior and in the outer regions of the nanoparticles. Such particles are also referred to hereinafter as "polyplexes".

The complexes and particles according to the invention can be characterized by their N/P ratio. This refers to the molar ratio of basic nitrogen atoms in the copolymer to the phosphate groups in the nucleic acid.

The N/P ratio in the particles according to the invention can vary in wide ranges. Typically, the N/P ratio in the particles according to the invention, is between 1 and 200, preferably between 2.5 and 100, more preferably between 5 and 50, and most preferably between 10 and 30.

Preferred particles according to the invention have diameters of up to 50 μm determined by DLS. Preferred are nanoparticles with diameters determined by means of DLS between 50 and 1000 nm.

Preferred particles according to the invention do not contain any auxiliary substances or additives, in particular no protective colloids and/or surfactants.

The particles containing polyplexes according to the invention can be prepared by precipitation. For this purpose, the cationic copolymers used according to the invention, which are hydrophilic due to the presence of polar groups depending on the pH value, are dissolved in water or in an aqueous buffer solution. A pH value of the aqueous solution of 3 to 6.5 is adjusted, for example by using an acetate buffer or another suitable buffer such as, for example, citrate buffer, lactate buffer, phosphate buffer and phosphate-citrate buffer. In addition, the nucleic acids are dissolved in water, the pH of the aqueous nucleic acid solution preferably being adjusted to a value between 6.5 and 8.5, particularly preferably to a value between 6.8 and 7.5. A buffer solution containing HEPES, TRIS, or salts only is particularly suitable for this purpose. Both solutions are combined, with the amounts of nucleic acids and of cationic copolymer being selected so that a desired N/P ratio is obtained. After mixing the two solutions, the mixture is agitated, for example for a short time, such as between 2 and 20 seconds. This can be done by stirring and/or by vortexing. Preferably, the resulting particles are allowed to stand for some time, such as between 5 and 20 minutes, before further use to allow binding between the polymer and nucleic acids. The particles according to the invention are precipitated in the dispersing medium in finely divided form.

In addition to the cationic copolymer and the nucleic acid, one or more auxiliary substances and additives may be present during their precipitation in the dispersing medium. Alternatively, these auxiliary substances and additives may be added after the nucleic acid-copolymer complex has been dispersed in the aqueous phase.

Water is used as the dispersing medium. Buffer substances, salts, sugars or acids and bases may be added to this to adjust the desired pH or osmolarity.

The particles according to the invention are excellently suited for gene transfer from cells, i.e. for introducing nucleic acids into cells. For this purpose, the particles containing nucleic acids are added to individual cells, tissues or a cell culture and taken up by the cells by endocytosis.

The invention also relates to the use of the particles described above for gene transfer into cells, i.e. for introducing nucleic acids into cells.

The following Examples illustrate the invention without limiting it.

Materials

All chemicals and solvents were purchased from commercial suppliers and used without further purification unless otherwise stated. 2-Ethyl-2-oxazoline (EtOx, 99+%) and triethylamine ($NEt_3$, 99.7%) were purchased from Acros Organics. 2-Ethyl-2-oxazoline was dried over calcium hydride and distilled under argon atmosphere. Methyl tosylate and (MeOTs, 98%) (98%) were obtained from Sigma Aldrich. Methyl tosylate was dried over barium oxide and distilled under argon atmosphere. Hydrochloric acid (37%) was obtained from Fisher Chemicals. Aqueous hydrogen peroxide solution (30% w/w) was obtained from Carl Roth. Acetyl chloride (approximately 90%) was obtained from Merck Schuchardt. Propionyl chloride (>98.0%), was purchased from Tokyo Chemical Industry (TCI). N, N-dimethylformamide (DMF) and acetonitrile were dried in a solvent purification system (MB-SPS-800 from M Braun).

Performance of Measurements

Proton ($^1H$) nuclear magnetic resonance (NMR) spectra were measured on a Bruker AC 300 MHz or a Bruker AC 400 MHz spectrometer. Measurements were performed at room temperature using either $D_2O$ or $d_4$-methanol as solvent. Chemical shifts (δ) are reported in parts per million (ppm) relative to the remaining non-deuterated solvent resonance signal. Infrared (IR) spectroscopy was performed on a Shimadzu IRAffinity-1 CE system equipped with a Quest ATR single reflectance diamond crystal cuvette for extended range measurements.

Size exclusion chromatography (SEC) was performed in N,N-dimethylacetamide (DMAc) using an Agilent 1200-series system equipped with a PSS degasser, a G1310A pump, a G1329A autosampler, a Techlab oven, a G1362A refractive index detector (RID), and a PSS GRAM-guard/30/1000 Å column (10 μm particle size). DMAc containing 0.21 wt % LiCl was used as the eluent. The flow rate was 1 ml min-1 and the oven temperature was 40° C. Polystyrene (PS) standards ranging from 400 to 1,000,000 g mol-1 were used to calculate molecular weights.

General Synthesis Methods

Synthesis of Poly(2-Ethyl-2-Oxazoline), PEtOx.

PEtOx was synthesized by cationic ring opening polymerization (CROP) of EtOx. In a scale-up batch method, MeOTs (124 g, 0.665 mol) and EtOx (3965 g, 40.00 mol, 60.2 equiv.) were dissolved under argon atmosphere in dry MeCN (5860 ml) in a 10 L Normag reactor to achieve a monomer-to-initiator ratio [M]:[I] of 60:1. After a reaction time of 6.5 h under reflux conditions, the polymerization was terminated with 270 ml of deionized water. After removal of aliquots for determination of monomer conversion (99.7%) by 1H NMR spectroscopy, the solvent was removed under reduced pressure, the residue was dissolved in dichloromethane (20 L) and washed with saturated aqueous sodium hydrogen carbonate solution (10 L) and aqueous sodium chloride solution (2×10 L). The organic phase was dried over a mixture of sodium sulfate (15 kg) and magnesium sulfate (4 kg) and the solvent was removed under reduced pressure. The product was finally dried in vacuo for 14 days (yield: 3848 g) and analyzed by 1H NMR spectroscopy (300 MHz, $D_2O$) and SEC. $M_{n,theor.}$=6000 g $mol^{-1}$; $M_{n,NMR}$=6300 g $mol^{-1}$; DP=60.

Synthesis of Linear Poly(Ethyleneimine), PEI.

The synthesis of PEI was performed by an adapted procedure based on previously published methods (Van Kuringen, H. P.; Lenoir, J.; Adriaens, E.; Bender, J.; De Geest, B. G.; Hoogenboom, R. Partial hydrolysis of poly(2-ethyl-2-oxazoline) and potential implications for biomedical applications? *Macromol. Biosci.* 2012, 12, 1114-1123; Tauhardt, L.; Kempe, K.; Knop, K.; Altuntaş, E.; Jäger, M.; Schubert, S.; Fischer, D.; Schubert, U. S. Linear polyethyleneimine: Optimized synthesis and characterization-On the way to “pharmagrade” batches. *Macromol. Chem. Phys.* 2011, 212, 1918-1924). PEtOx (80.0 g, 12.5 mmol) was dissolved in aqueous hydrochloric acid (6 M, 600 ml) and heated to 90° C. for 24 h. Volatiles were removed under reduced pressure and the residue was dissolved in deionized water (1600 ml). Aqueous NaOH (3 M, 300 mL) was added in portions to achieve a pH of 10, resulting in precipitation of the polymer. The polymer was then filtered off and purified by recrystallization in water (800 mL). PEI was obtained as a white solid (yield: 47.5 g).

$^1H$ NMR (300 MHz, CD3OD): degree of hydrolysis (DH)=99%.

Synthesis of Poly(Ethyleneimine-Stat-Glycine), oxPEI.

The synthesis of oxPEI was performed by an adapted method according to Englert et al. (Englert, C.; Hartlieb, M.; Bellstedt, P.; Kempe, K.; Yang, C.; Chu, S. K.; Ke, X.; García, J. M.; Ono, R. J.; Fevre, M.; Wojtecki, R. J.; Schubert, U. S.; Yang, Y. Y.; Hedrick, J. L. Enhancing the biocompatibility and biodegradability of linear poly(ethylene imine) through controlled oxidation. *Macromolecules* 2015, 48, 7420-7427). PEI (45.0 g, 17.0 mmol) was dissolved in methanol (1100 ml) with stirring and aqueous hydrogen peroxide solution (72 ml, 30% w/w, 0.7 equiv. per amine unit) was added dropwise. After stirring at room temperature for 3 days, the solvent was removed under reduced pressure and the product was dried in vacuo at room temperature for 7 days and at 70° C. for 1 day. oxPEI was obtained as a brown solid (yield: 29.1 g).

$^1H$ NMR (300 MHz, $D_2O$): Degree of oxidation (DO)=54%.

General Synthesis Method for Poly(2-n-Alkyl-2-Oxazoline-Stat-Glycine) s, dP(AOx-Co-EI).

oxPEI was predried under vacuum for 2 h at 70° C. and then dissolved in dry DMF (6 ml per g polymer) under argon atmosphere. Triethylamine (1 equiv. per amine unit) was added, followed by dropwise addition of acyl chloride solutions (0.5 equiv. per amine unit) in dry DMF (6 mL per g polymer). During this process, the mixture was cooled in an ice bath. Additional dry DMF (6 mL per g polymer) was used to rinse residues from the flask walls. After reaching room temperature, the reaction mixture was stirred for an additional 24 hours. Purification was adjusted depending on the solubility of the products. Details of the preparation of individual dP(AOx-co-EI) can be found in the experimental section below.

Determination of the Degree of Hydrolysis

The degree of hydrolysis DH was calculated according to equation (1) from the integrals of the $^1H$ NMR spectra of PEI. Here, D means the integral of the methylene groups of the ethyleneimine units and A means the integral of the methyl groups of the remaining EtOx units.

$$DH = \frac{D}{D + \frac{4}{3}A} \cdot 100\% \quad (1)$$

Determination of the Degree of Oxidation

The degree of oxidation DO was calculated from the integrals of the polymer backbone signals of the $^1$H NMR spectra of oxPEI according to equation (2). Here, F means the integral of the methylene group of the glycine units, A means the integral of the methyl groups of the remaining EtOx units and D means the integral of the methylene groups of the ethyleneimine units.

$$DO = \frac{2\left(F - \frac{4}{3}A\right)}{\left(F - \frac{4}{3}A\right) + D} \cdot 100\% \quad (2)$$

Performance of Titration

Titrations for the determination of the remaining amino groups were carried out with an auto-mated Metrohm OMNIS Titrator equipped with a Metrohm Ecotrode plus pH electrode. All measurements were performed in a dynamic titration mode that adapted the titration speed to the change in pH during the titration. A typical measurement was performed as follows: The polymer was dissolved in deionized water to give a polymer solution with a concentration of 3 mg $ml^{-1}$. The polymer solution was acidified by adding a semi-concentrated aqueous HCl solution dropwise to achieve a pH of 2. The solution was then titrated to a pH of 12 with stirring against aqueous 0.1 M sodium hydroxide solution. The equivalence points were determined from the first derivative of the titration curve.

Performance of Degradation Studies

For degradation under acidic conditions, the polymer (20 mg) was dissolved in 6 mol $L^{-1}$ HCl (2 ml) and stirred for 48 h at 90° C. The reaction mixture was neutralized with aqueous sodium hydroxide solution and the water was removed under reduced pressure.

Preparation Example H1: Synthesis of Poly(2-Methyl-2-Oxazoline-Co-Ethyleneimine-Co-Glycine), dP(MeOx-Co-EI)

$P(MeOx\text{-}co\text{-}EI)_6$ was prepared according to the general procedure using 500 mg oxPEI, 614 µl (446 mg, 4.41 mmol, 1 equiv. per amine unit) triethylamine and 157.2 µl (173 mg, 2.20 mmol, 0.5 equiv. per amine unit) acetyl chloride. The precipitated triethylammonium salt was filtered off after the reaction and the filtrate was concentrated under reduced pressure The crude product was dissolved in methanol and precipitated three times in ice-cold diethyl ether (about-80° C.). Dissolution in deionized water, freeze-drying and drying in vacuum at 40° C. gave dP(MeOx-co-EI) as a brown solid (yield: 406 mg).

Preparation Example H2: Synthesis of Poly(2-Ethyl-2-Oxazoline-Co-Ethyleneimine-Co-Glycine), dP(EtOx-Co-EI)

P(EtOx-co-EI) was prepared according to the general procedure using 500 mg oxPEI, 614 µl (446 mg, 4.41 mmol, 1 equiv. per amine unit) triethylamine, and 192.2 µl (204 mg, 2.20 mmol, 0.5 equiv. per amine unit) propionyl chloride. Triethylammonium chloride formed during the reaction was filtered off and the solution was concentrated under reduced pressure. The residue was dissolved in methanol and precipitated eight times in ice-cold diethyl ether (about −80° C.). The crude product was dissolved in deionized water and freeze-dried. After drying in vacuum at 40° C., dP(EtOx-co-EI) was obtained as a brown solid (yield: 415 mg).

Example C1: Characterization of the Polymers by $^1$H-NMR Spectroscopy

The first step was to synthesize a significant amount of PEtOx as a well-defined starting material via CROP (compare General Synthesis Methods, Synthesis of PEtOx). To this end, a synthesis protocol was developed in a 10 L Normag reactor that yielded nearly 4 kg of PEtOx with a degree of polymerization (DP) of 60 and a narrow dispersity (Đ) of 1.14, as determined by SEC in DMAc. Since CROP was terminated by addition of water, the resulting PEtOx contained two isomeric end groups resulting from nucleophilic attack on the 2- or 5-positions of the oxazoline ring, but in both cases this resulted in hydroxyl end groups upon hydrolysis to linear poly(ethyleneimine) (PEI). The hydrolysis was carried out under acidic conditions (compare general synthesis methods, synthesis of PEI). To obtain complete hydrolysis, the reaction was carried out overnight with an excess of 6 M HCl. The successful synthesis was confirmed by the 1H NMR spectrum, which clearly showed the disappearance of the signals assigned to the ethyl substituents of PEtOx. Moreover, a clear high-field shift of the backbone signal confirmed the formation of PEI. The degree of hydrolysis (DH) was determined to be 99%, calculated by the ratio of the integrals in the $^1$H NMR spectrum (compare general synthetic methods, synthesis and characterization of dP(AOx-co-EI), equation (1)).

Next, oxPEI was prepared by oxidation of PEI using hydrogen peroxide as oxidant. The oxidation occurred in the polymer backbone, thus forming randomly distributed backbone amide groups. The structure of the resulting oxPEI corresponds to the repeating unit of poly(glycine) adjacent to unaffected ethyleneimine units. Therefore, the polymer can also be referred to as a poly(ethyleneimine-stat-glycine) copolymer. With the aim of generating 50% of the amino groups by oxidation in PEI, 0.7 equivalents of hydrogen peroxide per amino group were used. The degree of oxidation (DO), determined by the integral ratio in the 1H NMR spectrum as 54% (compare General Methods of Synthesis, Synthesis and Characterization of dP(AOx-co-EI), Eq. (2)), confirmed the successful synthesis. The methylene group signals associated with the ethyleneimine and glycine repeating units occurred in close proximity in the $^1$H NMR spectrum and partially overlapped each other The NH proton signal indicated the formation of an amide group, which confirmed the presence of glycine units as well.

Since the remaining amino groups can be further functionalized, the resulting oxPEI provided the platform for the synthesis of various degradable polymers. Here, subsequent reacylation with the aliphatic acyl chlorides acetyl chloride and propionic acid chloride was used to reintroduce amide units equivalent to the N-acylethylenimine structures in PAOx. The resulting polymer structures resemble PAOx with additional, randomly distributed poly(glycine) units and polyethyleneimine units integrated into the polymer backbone. Therefore, they can also be considered as poly (2-n-alkyl-2-oxazoline-stat-ethyleneimine-stat-glycine) copolymers or, due to the degradability of the glycine unit, as degradable poly(2-alkyl-2-oxazoline-stat-ethyleneimine)

analogs. Thus, the described synthetic approach allowed the preparation of polymers with the same chain length and DO, using only EtOx as a commercially available monomer.

Characterization of the purified dP(AOx-co-EI) by $^1H$ NMR spectroscopy indicated a decrease in the signals attributed to the PEI repeating units, while signals attributed to the alkyl side chains confirmed their partial conversion to the corresponding N-acylethylenimine structures.

Example C2: Characterization of the Polymers by IR-Spectroscopy

Further structural evidence was obtained by IR spectroscopy. FIG. 1 shows ATR-IR spectra of dP(MeOx-co-EI) and dP(EtOx-co-EI) in the range of wavenumbers from 600 to 4000 $cm^{-1}$ including assignment of the major bands. The IR spectroscopy of PEtOx, PEI, poly(glycine) as well as oxPEI was previously described in the literature, which allowed easy assignment of vibrational bands. The band at 3235 and 3246 $cm^{-1}$ can be attributed to the NH vibration of the amino group. The vibrational band at 1647 and 1650 $cm^{-1}$ can be attributed to the amide I band, which is mainly due to the carbonyl valence vibration. The band disappeared almost completely during hydrolysis to PEI due to cleavage of the side chain carrying carbonyl groups. During oxidation to oxPEI and subsequent reacylation to dP(EtOx-co-EI), amide groups were reintroduced, leading to an increase in the carbonyl vibrational band. The amide II band at 1543 $cm^{-1}$, mainly caused by the NH bond deformation vibration, was not observed in PEtOx, which had only tertiary amide groups without NH bonds, and showed the structural difference between PEtOx and dP(MeOx-co-EI) or dP(EtOx-co-EI). Signals from carboxylic acid derivatives due to possible degradation products are expected at about 1710 $cm^{-1}$. However, such signals could not be observed in the spectra of oxPEI or dP(MeOx-co-EI) or dP(EtOx-co-EI), respectively.

Example C3: Characterization of the Polymers by SEC

Figure 2:
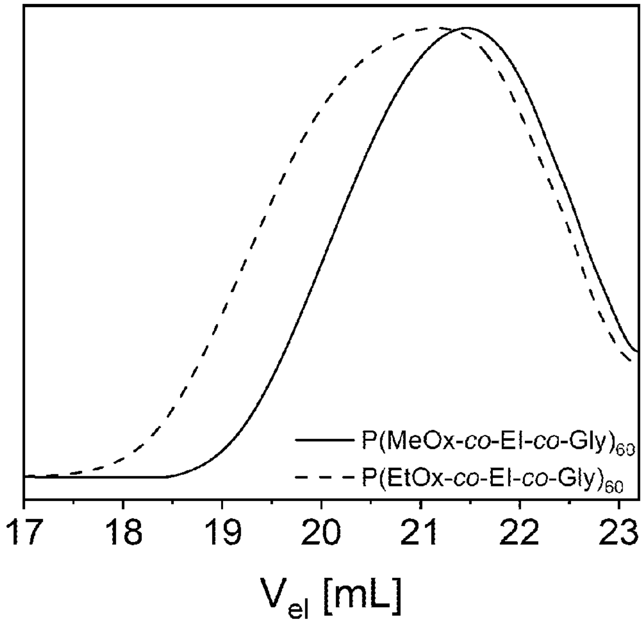
FIG. 2 is a graph of SEC elugrams of dP(MeOx-co-EI) and dP(EtOx-co-EI) as described in Example C3.

An overlay of the SEC elugrams of the two polymers in DMAc is shown in FIG. 2. dP(EtOx-co-EI)($M_n$=2700, Đ=1.72) was shifted to lower elution volumes and thus higher molecular weights compared to dP(MeOx-co-EI) ($M_n$=2200, Đ=1.51).

Example C4: Characterization of the Polymers by Titration

Figure 3:
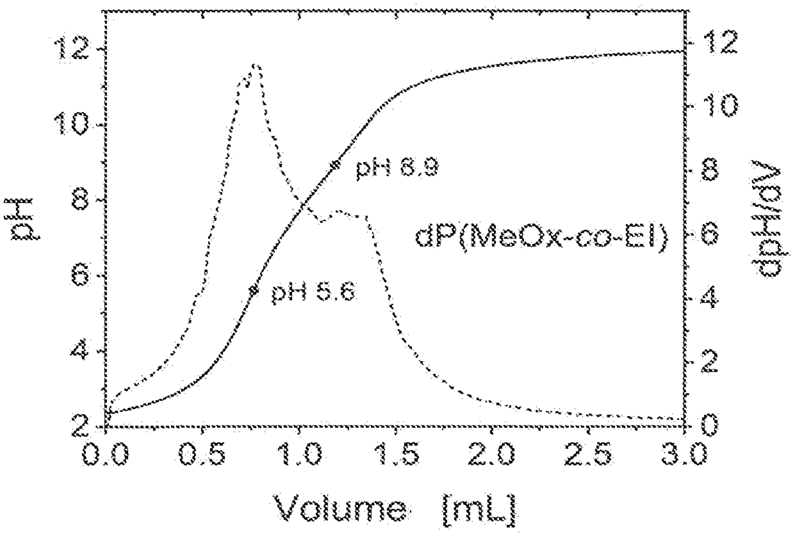
FIG. 3 is a graph of titration curves of dP(MeOx-co-EI) as described in Example C4.
Figure 4:
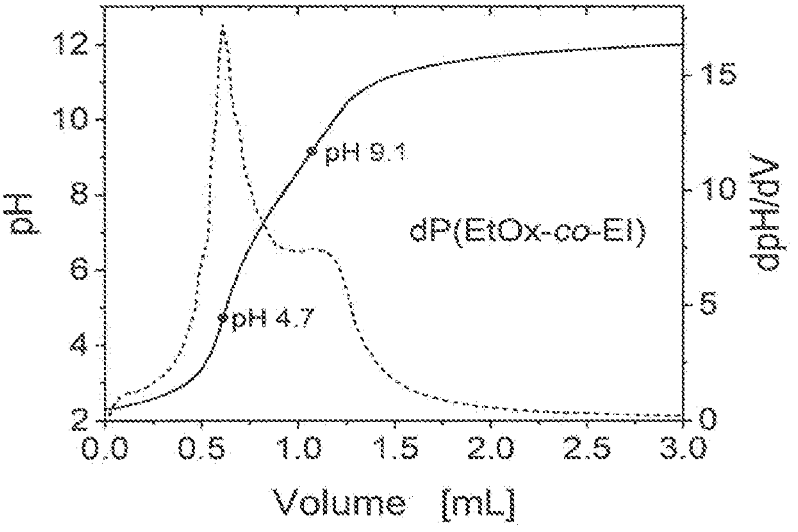
FIG. 4 is a graph of titration curves of dP(EtOx-co-EI) as described in Example C4.

Both polymers could be dissolved in water at room temperature. Titrations in aqueous solution were performed to confirm the presence of the amino groups in the polymer backbone. Although the titration of amino groups allowed a qualitative evaluation, an accurate quantitative analysis was not performed due to water residues that would affect the results. The titration curves of dP(MeOx-co-EI) and dP(EtOx-co-EI) are shown along with their respective first derivatives in FIGS. 3 and 4. The polymer solutions were acidified with semi-concentrated HCl prior to titration. The corresponding pH values of the equivalence points are also shown. Acidification of the aqueous polymer solutions with semi-concentrated HCl prior to the titrations resulted in the appearance of two equivalence points (EP) for polymers containing amino groups when titrated with dilute sodium hydroxide solution. The first EP corresponds to the neutralization of the HCl excess, while the second EP refers to the neutralization of the amino groups. Two EPs were observed in the titration curves of dP(MeOx-co-EI) and dP(EtOx-co-EI), which can be attributed to the amino groups remaining after the proportional functionalization of oxPEI.

Example C5: Characterization of the Polymers by Degradation Studies by Means of Acidic Hydrolysis An important advantage of dP(AOx-co-EI) compared to PAOx is their ability to be potentially degradable due to the additional backbone amide groups. To confirm this, dP(MeOx-co-EI) and dP(EtOx-co-EI), were treated with 6 M HCl at 90° C. for 2 days. These conditions are similar to those used for the hydrolysis of PEtOx to PEI, where no degradation of the PEtOx or PEI polymer backbone occurs.

Figure 5:
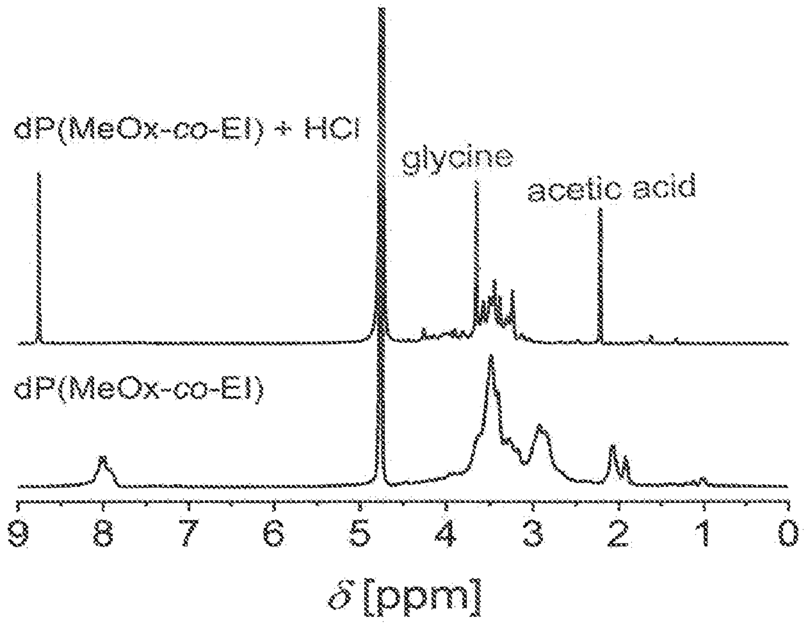
FIG. 5 is a graph of 1H NMR spectra of dP(MeOx-co-EI) before and after acid hydrolysis as described in Example C5.
Figure 6:
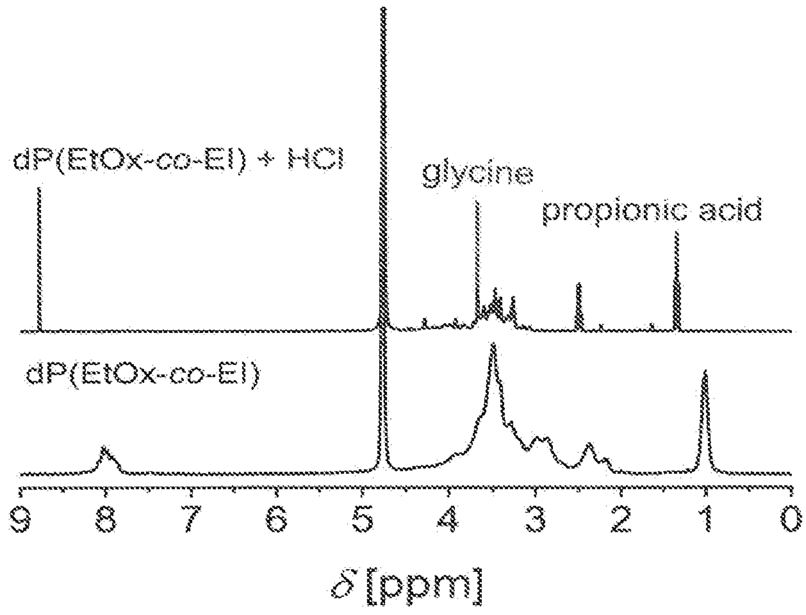
FIG. 6 is a graph of 1H NMR spectra of dP(EtOx-co-EI) before and after acid hydrolysis as described in Example C5.

FIGS. 5 and 6 show the overlays of the 1H NMR spectra of dP(MeOx-co-EI) and dP(EtOx-co-EI) before (lower spectrum) and after (upper spectrum) treatment with HCl. The individual spectra are superimposed vertically for clarity.

FIGS. 5 and 6 show the successful degradation of the polymers under these conditions. Before treatment with HCl, the polymers showed broad signals typical of polymers, while the signals of the degraded polymer were sharp, as is usually observed for small molecules.

The splitting of the EtOx side chain signals of dP(EtOx-co-EI) at 1.34 ppm and 2.49 ppm into a triplet and a quartet, respectively, indicated the cleavage of the side chain from the polymer backbone, yielding propionic acid. This did not necessarily confirm the degradation of the polymer chain itself and was also found for PEtOx upon treatment with HCl. However, while the spectra of PEtOx after treatment showed only the backbone signal of the remaining PEI, several sharp signals appeared at chemical shifts of the former dP(EtOx-co-EI) backbone. The singlet at 3.67 ppm can be attributed to the methylene unit of glycine formed upon degradation, while the triplets in the range of 3.65 ppm and 3.21 ppm can be attributed to the remaining ethyleneimine units. In addition, a sharp signal appeared at 8.77 ppm, which had already been reported for oxPEI after degradation and which could be due to additional degradation products. At the same time, the broad amide signal disappeared at about 8.0 ppm, indicating hydrolysis of the associated backbone amide groups. The superposition of the spectra of dP(MeOx-co-EI) before and after treatment with HCl showed similar behavior. Cleavage of the side chain as acetic acid gave a singlet at 2.17 ppm. Furthermore, cleavage of the broad polymer backbone signals showed a sharp singlet at 3.61 ppm, which can be assigned to glycine as described above. Several triplets in the range of 3.58 to 2.95 ppm were those attributable to degradation products of the ethyleneimine units.

The invention claimed is:

1. Copolymers containing 15 to 60 mol % of structural units of formula (I), 10 to 60 mol % of structural units of formula (II) and 25 to 75 mol % of structural units of formula (III)

$$—NR^1—CHR^3—CHR^4— \quad (I),$$

$$—NH—CO—CHR^7— \quad (II),$$

$$—NH—CHR^9—CHR^{10}— \quad (III),$$

wherein $R^1$ is a radical of the formula $—CO—R^2$, of the formula $—CO—NH—R^2$, of the formula $—CH_2—CH(OH)—R^{12}$ or of the formula $—CH_2—CH(NH_2)—R^{12}$, $R^3$, $R^4$, $R^7$, $R^9$ and $R^{10}$ independently of one another are hydrogen, methyl, ethyl, propyl or butyl, $R^2$ is selected from the group consisting of hydrogen, alkyl, cycloalkyl, aryl, aralkyl, $—C_mH_{2m}—X$ or $—(C_nH_{2n}—O)_o—(C_pH_{2p}—O)_q—R^6$, $R^6$ is hydrogen or $C_1$-$C_6$ alkyl, $R^{12}$ is selected from the group consisting of hydrogen, alkyl, alkenyl, cycloalkyl, aryl or aralkyl, X is selected from the group consisting of hydroxyl, alkoxy, amino, N-alkylamino, N,N-dialkylamino, heterocyclyl having at least one ring nitrogen atom, guanidino, carboxyl, carboxylic acid ester, sulfuric acid ester, sulfonic acid ester or carbamic acid ester, m is an integer from 1 to 18, n and p independently of one another are integers from 2 to 4, where n is not equal to p, and and g independently of one another are integers from 0 to 60, at least one of o or q not being equal to 0, wherein said mol % of structural units are each based on the total amount of the structural units of the formula (I), (II) and (III).

2. The copolymers according to claim 1, wherein $R^1$ is a radical of formula $—CO—R^2$.

3. The copolymers according to claim 1, wherein $R^2$ is $C_1$-$C_{18}$-alkyl.

4. The copolymers according to claim 1, wherein n=2 and p=3.

5. A method of using the copolymers according to claim 1 for the manufacture of formulations containing pharmaceutical or agrochemical active ingredients.

6. Particles comprising copolymers according to claim 1.

7. The particles according to claim 6, wherein these are present as nanoparticles with an average diameter $D_{50}$ of less than 1 μm.

8. Complexes comprising a copolymer according to claim 1 and compounds with anionic groups.

9. Particles comprising complexes according to claim 8.

10. The p articles according to claim 9, wherein these have a N/P-ratio between 1 and 200.

11. A method of using the particles according to claim 9 for gene transfer into cells.

12. The copolymers according to claim 3, wherein $R^2$ is $C_1$-$C_6$-alkyl.

13. The particles according to claim 7, wherein the average diameter $D_{50}$ is from 20 to 500 nm.

14. The complexes according to claim 8, wherein the compounds with anionic groups are nucleic acids.

15. The particles according to claim 10, wherein the N/P-ratio is between 2.5 and 100.

16. A process for the preparation of copolymers according to claim 1 comprising the steps of:

i) reacting a polyalkyleneimine containing recurring structural units of formula (Ia) with an oxidizing agent, thereby obtaining a copolymer containing the structural units of formula (Ia) and of formula (II)

$$—NH—CR^3H—CR^4H— \quad (Ia),$$

$$—NH—CO—CR^7H— \quad (II),$$

wherein $R^3$, $R^4$, $R^5$, and $R^7$ and $R^8$ have the meaning are as defined in claim 1, and ii) reacting the copolymer of step i) with an acyl derivative of the formula (VII) or with an isocyanate of the formula (VIII) or with an epoxide of the formula (IX) or with an aziridine of the formula (X) to give a copolymer according to claim 1, $$R^2—CO—R^{13}, \quad (VII)$$

$$R^2—NCO, \quad (VIII)$$

(IX)

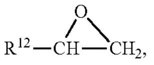

(X)

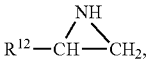

wherein $R^2$ and $R^{12}$ are as defined in claim 2 and $R^{13}$ represents a leaving group.

17. The process for the preparation of copolymers according to claim 1 comprising the steps of:

iii) partially hydrolyzing a polyoxazoline containing recurring structural units of formula (I)

$$—NR^1—CHR^3—CHR^4— \quad (I),$$

to give a copolymer containing the recurring structural units of formula (I) and of formula (III)

$$—NH—CHR^9—CHR^{10}— \quad (III),$$

wherein $R^1$, $R^3$, $R^4$, $R^5$, $R^9$, and $R^{10}$ and $R^{11}$ have the meaning are as defined in claim 1, and iv) reacting the copolymer from step iii) with an oxidizing agent, thereby obtaining a copolymer containing the structural units of formula (I), of formula (II) and of formula (III)

$$—NH—CO—CHR^7— \quad (II),$$

wherein $R^7$ is as defined in claim 1.

18. The process according to claim 16, wherein the oxidizing agent used is a peroxide, hydroperoxide or a percarboxylic acid.

19. The process according to claim 16, wherein the polyalkyleneimine used in step i) is obtained by acidic hydrolysis of a poly(oxazoline).

20. The process according to claim 16, wherein $R^{13}$ is fluorine, chlorine, bromine, iodine, or an activated carboxylic acid derivative.

* * * * *